United States Patent [19]

Prutchi et al.

[11] Patent Number: 5,713,935
[45] Date of Patent: Feb. 3, 1998

[54] METHOD AND APPARATUS FOR MONITORED BIPHASIC CARDIAC IMPEDANCE SENSING

[75] Inventors: David Prutchi; Patrick J. Paul, both of Lake Jackson; D. Curtis Deno, Missouri City, all of Tex.

[73] Assignee: Sulzer Intermedics Inc., Angleton, Tex.

[21] Appl. No.: 697,454

[22] Filed: Aug. 23, 1996

[51] Int. Cl.6 ................................................. A61N 1/37
[52] U.S. Cl. ....................................................... 607/28
[58] Field of Search .............................. 607/6, 8, 9, 24, 607/28; 128/697

[56] References Cited

U.S. PATENT DOCUMENTS

| | | | |
|---|---|---|---|
| 4,140,132 | 2/1979 | Dahl | 128/419 |
| 4,291,699 | 9/1981 | Geddes | 178/419 |
| 4,688,573 | 8/1987 | Alt | 128/419 |
| 4,702,253 | 10/1987 | Nappholz et al. | 128/419 |
| 5,137,019 | 8/1992 | Pederson | 128/419 |
| 5,174,286 | 12/1992 | Chirife | 128/419 |
| 5,201,808 | 4/1993 | Steinhaus et al. | 128/419 |
| 5,271,395 | 12/1993 | Wahlstrand et al. | 607/9 |
| 5,391,190 | 2/1995 | Pederson | 607/23 |
| 5,507,785 | 4/1996 | Deno | 607/24 |
| 5,534,018 | 7/1996 | Wahlstrand et al. | 607/28 |
| 5,540,724 | 7/1996 | Cox | 607/28 |

*Primary Examiner*—William E. Kamm
*Attorney, Agent, or Firm*—John R. Merkling

[57] ABSTRACT

A method and apparatus for monitoring balanced biphasic current pulses used for measuring impedance in cardiac stimulators involves detecting imbalances between the pulses of opposite polarity. Such imbalances are potentially harmful to cardiac stimulator users. By converting the two different pulse phases into potentials, a determination can be made as to whether adequately balanced pulses are being generated. If an imbalance is detected, corrective action can be taken quickly enough to avoid harmful effects to the stimulator user.

26 Claims, 5 Drawing Sheets

METHOD AND APPARATUS FOR MONITORED BIPHASIC CARDIAC IMPEDANCE SENSING

TECHNICAL FIELD

Our invention relates to the use of biphasic signals for cardiac impedance sensing and more particularly to cardiac pacemakers with monitored biphasic impedance sensing.

BACKGROUND OF OUR INVENTION

Implanted cardiac pacemakers are employed to assist patients suffering from severe bradycardia or chronotropic incompetence. Originally, such pacemakers restored a normal, at rest, heart rate by providing either a fixed rate or a narrow range of externally programmable rates. However, these pacemakers failed to meet patients' metabolic demands during exercise. Consequently, so-called "rate adaptive" or "rate responsive" pacemakers were developed. These pacemakers sense some parameter correlated to physiologic need and adjust the pacing rate of the pacemaker accordingly.

Numerous parameters have been selected to attempt to correlate pacing rate to the actual physiologic need of the patient. Blood pH, blood temperature, QT interval, vibration, respiration rate, or accelerations due to physical activity have been employed with varying degrees of success. Also, the stroke volume of the heart and the minute volume of respiration may be inferred from impedance measurements. The stroke volume of the heart is defined as the volume of blood expelled by the ventricle in a single beat. It is equal to the difference between the end diastolic volume and the end systolic volume. In normal human subjects with healthy hearts, the stroke volume of the heart has been found to remain relatively constant over a wide range of exertion. Increases in cardiac output required to meet physiologic needs are primarily provided by increased heart rate. The heart may attempt to increase its stroke volume during exertion. The stroke volume cannot increase, however, by a factor of more than about two or two and half times. Increasing the pacing rate is therefore still desired. One may utilize the body's tendency to attempt to increase stroke volume to adjust the pacing rate of an implanted pacemaker, thereby providing an appropriate physiologic pacing rate.

Various pulse-based impedance sensors have been proposed or are now in use with cardiac stimulators for deriving hemodynamic and other physiologic parameters. These sensors deliver trains of fairly low-energy probing pulses between two or more electrodes of a pacing or defibrillation lead system. Each train contains pulses delivered at the rate of 1 to 500 per second. In general, these pulses have a biphasic morphology in order to balance the charge delivered to tissue, thus avoiding ion migration and electrolysis within the living tissue, as well as reducing interference on external monitoring equipment. In addition, charge balancing reduces the possibility of actually capturing the heart muscle with low-threshold leads.

The impedance sensor may be implemented as described by Salo et al. in U.S. Pat. No. 5,190,035 by injecting a relatively low frequency carrier signal (under 5 KHz) between spaced electrodes disposed within the body. The beating action of the heart and movement of the chest (because of respiration) modulate this carrier due to changes in sensed impedance between electrodes implanted within the body. Similar approaches have been described in a number of patents, for example by Geddes in U.S. Pat. No. 4,291,699 and Pederson et al. in U.S. Pat. Nos. 5,137,019 and 5,391,190.

Carrier-based impedance sensors use a relatively high amount of electrical energy, and thus pulse-based methods have been introduced to minimize energy utilization. For example, Chitire, in U.S. Pat. No. 5,174,286, describes an impedance sensor which derives a signal for the control of a cardiac stimulator from the impedance measured between two electrodes in the lead system using a limited number of sub-threshold pacing pulses. Other pulse-based systems, such as those described by Nappholz et al. (U.S. Pat. No. 5,201,808) inject trains of either monophasic or asymmetrical biphasic probe pulses to measure impedance.

U.S. Pat. No. 5,507,785, to Deno (expressly incorporated by reference herein) describes an impedance sensor which injects trains of charge-balanced symmetrical biphasic current pulses between two electrodes of a pacing lead system. The resulting voltage difference is then synchronously sampled in order to measure impedance or transimpedance. By producing balanced, symmetrical pulses, the possibility of actually capturing the heart muscle with low-threshold leads is drastically reduced.

A hardware or software failure, however, could result in the generation of a train of imbalanced biphasic or monophasic pulses. There are few stimuli better at eliciting ventricular fibrillation than pulses at 50–200 Hz. The very lowest threshold leads might actually pace when delivering a single phase (or imbalanced) pulse at low currents (e.g. 1 mA) and shod duration (in the tens of microseconds range). Just a few seconds of stimulation in this case would lead to ventricular fibrillation which does not revert to sinus rhythm when recognized and stimulation is discontinued.

For this reason, we recognized that it is desirable to verify the charge balance of biphasic current pulses. This avoids injecting probe pulses which are potentially dangerous to the patient.

SUMMARY OF OUR INVENTION

We have invented a monitor for an implantable pacemaker that uses impedance measurements to achieve heart rate responsive operation. Impedance changes are measured as an indicator of cardiac stroke volume or minute volume. A signal injector produces balanced biphasic current pulses which are delivered across a selected set of electrodes. A detector senses the voltage resulting from the applied biphasic current pulses in each phase.

A number of circuit or software failures can cause the biphasic current pulse pair to become unbalanced. This imbalance may cause deleterious charging effects. Where the imbalance is sufficiently severe, it may cause ventricular fibrillation.

By monitoring the pulse pair to determine, for example, if the amplitude and duration of the pulses making up each pair are substantially balanced, corrective action can be taken to avoid deleterious effects. The injector pulse may be continuously monitored so that corrective action can be taken immediately. Alternatively, the monitoring action can be done periodically, but with sufficient frequency to allow timely corrective action.

In accordance with another embodiment, charge balance may be assessed in association with an internal impedance load. Monitoring may then proceed either independently of or coincident with clinical impedance measurements.

The monitoring operation may be accomplished by producing voltage signals which are representative of the charging effect of each current pulse phase. These voltage signals can be added, compared, or subtracted to provide an indication of the extent of balance between pulses of opposite polarity.

Thus it is an object of the present invention to provide a monitor which is capable of initiating corrective action in timely fashion in response to the loss of substantial balance between injected current pulses of opposite polarity. It is highly desirable to achieve an added level of safety in connection with the use of balanced biphasic current pulses for measuring cardiac impedance in a rate responsive cardiac stimulator.

DETAILED DESCRIPTION OF OUR PREFERRED EMBODIMENTS

We will now describe the preferred embodiment of our invention with reference to the accompanying figures. Like numerals will be used to designate like parts throughout.

Figure 1:
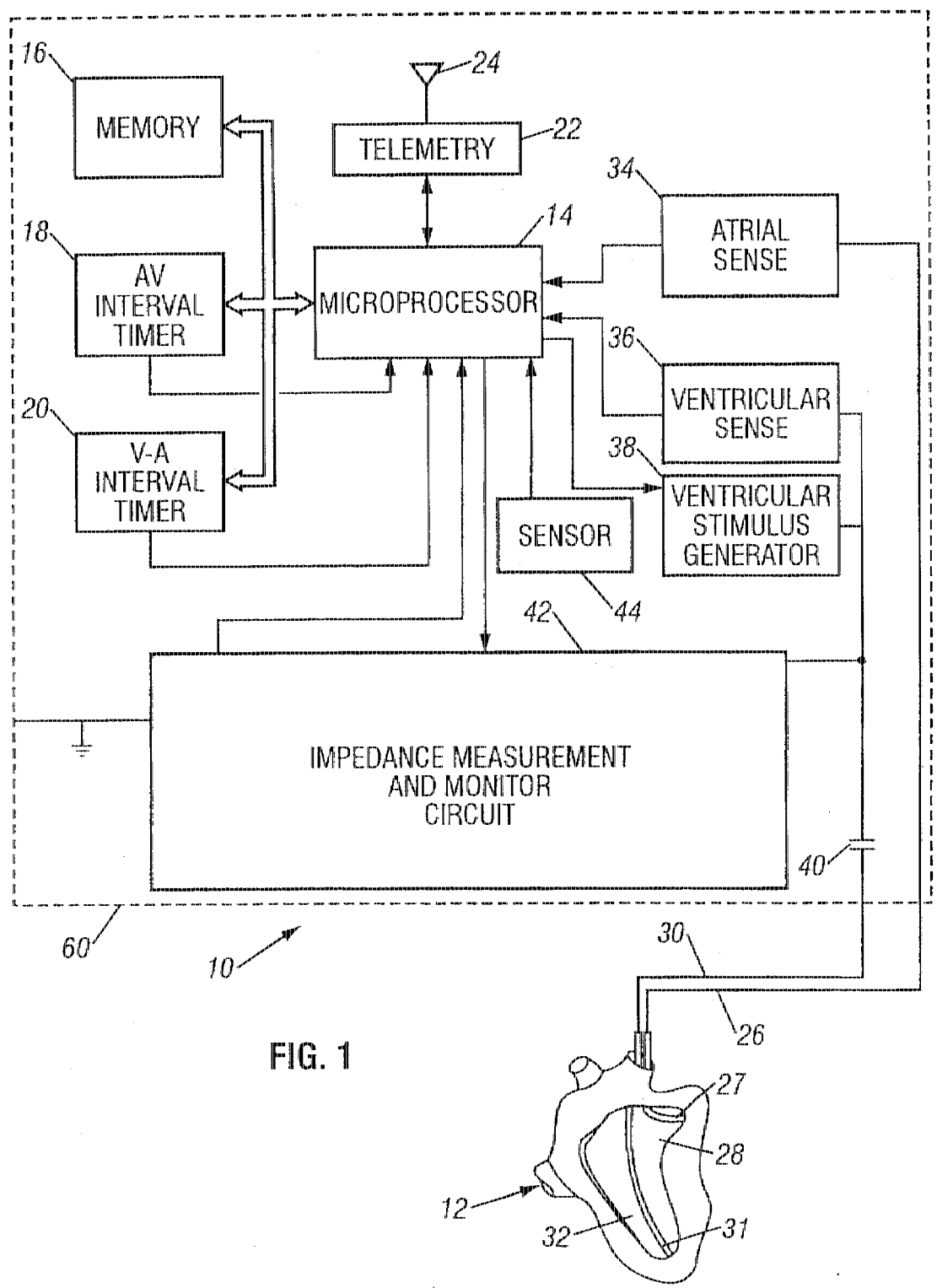
FIG. 1 is a block diagram of a rate adaptive pacemaker according to an embodiment of our invention.

Referring now to FIG. 1, a pacemaker, generally designated 10, is illustrated in schematic fashion with connection to a human heart 12. For ease of illustration, we have elected to describe our invention in connection with a pacemaker having atrial sensing and ventricular sensing and pacing. It should be understood, however, that our invention can be employed in connection with an apparatus for sensing in the atrium, the ventricle or both and that both atrial or ventricular pacing or either of them could be provided without departing from the teachings of our invention. Our invention could also be implemented in an apparatus that includes an implantable defibrillator/cardioverter.

With this understanding, the illustrated pacemaker 10 comprises a microprocessor 14 which executes various control programs to regulate the action of the pacemaker. The microprocessor 14 is connected to additional memory 16 for the storage of programs and data as may be needed. As is known in the art, one or more internal clocks may be provided to permit timing of various events. For example, an A-V interval timer 18 may be provided. Similarly, a V-A interval timer 20 may also be provided, as known in the art. The microprocessor is provided with a telemetry circuit 22 to enable communication, across an antenna 24, with an external programmer (not shown). Telemetry permits an attending physician to obtain data and information from the pacemaker and to set various selectable pacemaker control parameters, as known in the art.

The pacemaker 10 is connected to the heart 12 through a first lead 26 to an electrode 27 in the atrium 28 and through a second lead 30 to an electrode 31 in the ventricle 32. An indifferent electrode (e.g., the pacemaker can) is provided to complete the electrical circuit through the body. In the illustrated embodiment, a can or outer casing 60 of the pacemaker serves as the indifferent electrode. Bipolar leads can also be used with our invention as well as the unipolar leads illustrated here. Atrial electrogram sensing, through an atrial sense circuit 34, and ventricular sensing, through a ventricular sense circuit 36, provide information to the microprocessor concerning the condition and responsiveness of the heart. In addition, pacing pulses are provided to the ventricle from a ventricular stimulus generator 38. It is clearly within the scope of those skilled in the art to provide cardioversion/defibrillation capabilities in response to the detected condition of the heart. Stimulation to the heart is passed through a coupling capacitor 40.

To control the pulse rate of the ventricular stimulus generator 38, the microprocessor 14 acquires information on the condition of the heart through an impedance circuit 42. The impedance circuit 42 detects changes in impedance, for example, due to the changing shape of the heart as it beats and pumps blood. This information can be used to derive a measure of the stroke volume or ejection fraction or end diastolic volume of the heart. Futhermore, the shape of the impedance waveform can provide information on other cardiac timing parameters such as isovolumetric contraction time or pre-ejection period. The impedance circuit 42 includes monitoring to insure that substantially balanced biphasic pulses are being produced by the impedance circuit 42.

Sensor 44 may also be provided to obtain an indication of physiologic need and to adjust the pacing rate. Such a sensor may be an accelerometer, as described by Dahl, U.S. Pat. No. 4,140,132, (incorporated herein by reference) a temperature sensor, as described by Alt, U.S. Pat. No. 4,688,573 (also incorporated herein by reference), or any other suitable sensor of a parameter which may be correlated to physiologic need of the patient.

Figure 2:
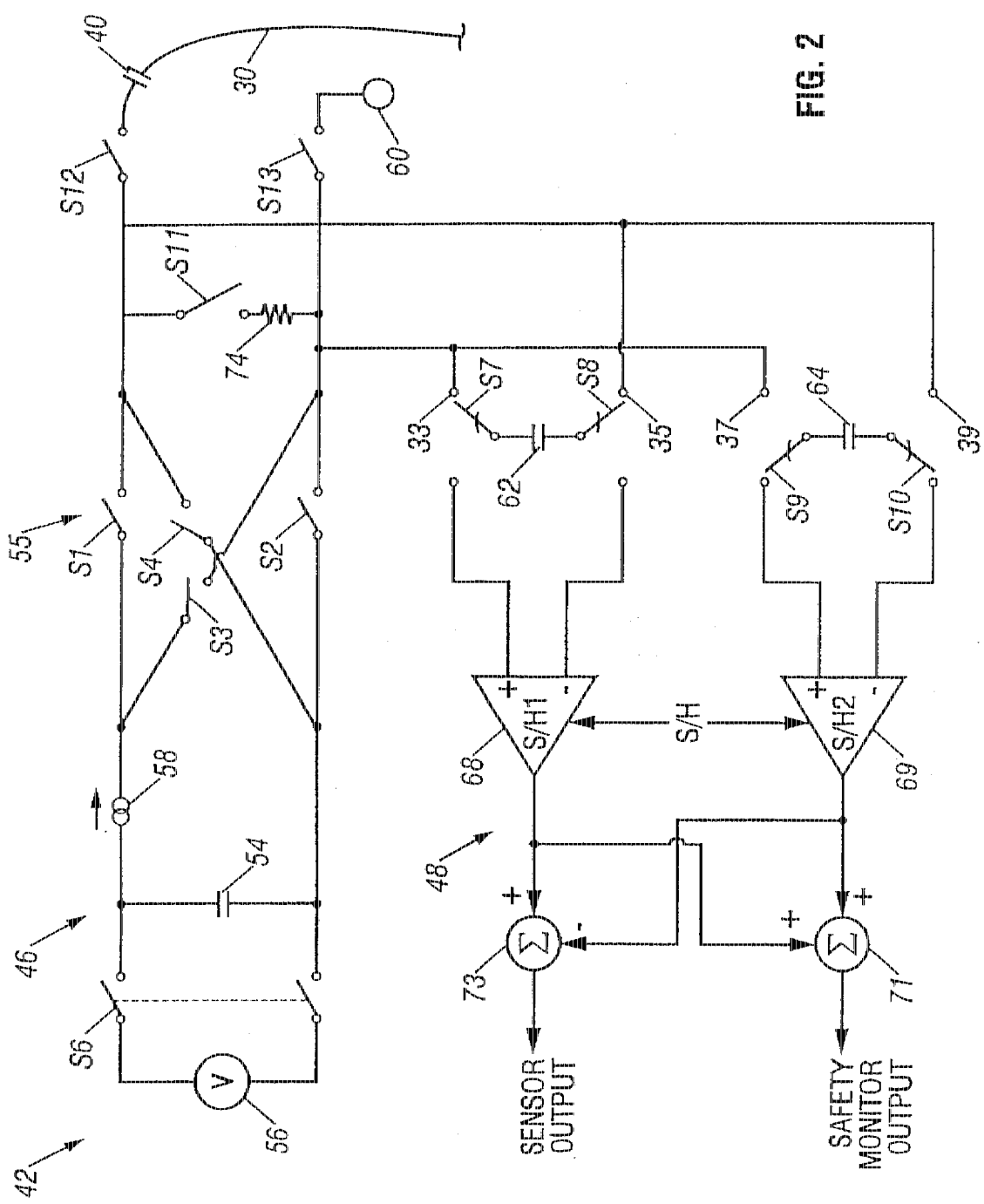
FIG. 2 is a circuit diagram showing an impedance measuring circuit with monitoring in accordance with our invention.

An impedance circuit 42, shown in FIG. 2, comprises a biphasic signal injector 46 and a signal detector 48. The biphasic signal injector 46 can produce short, essentially symmetrical biphasic constant current pulses to detect the varying impedance of the heart. Each pulse may have an exemplary duration on the order of one to fifty microseconds and an exemplary amplitude of from 0.1 to 2 mA. The resulting detected voltage across the heart will be on the order of 50–1000 mV.

Figure 3:
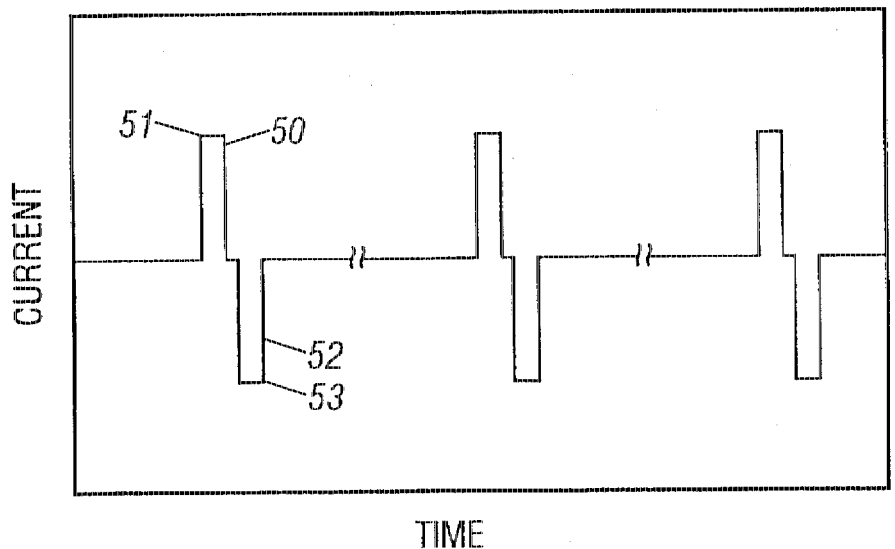
FIG. 3 shows an idealized plot of current versus time for an exemplary series of biphasic pulses that are useful in our invention.

As shown in FIG. 3, the two pulses forming a pulse pair may be substantially similar in duration and magnitude, polarity being reversed. The differences in magnitude and duration between a first pulse 50 and a second pulse 52 could be no more than plus or minus ten percent. Most advantageously, pulse amplitude is very similar, on the order of less than 0.1% variation. Greater variability in duration may acceptable. Also, the pulses could assume shapes other than the rectangular shape shown in FIG. 3. For example, the leading and trailing edges may be rounded in some applications.

While the symmetrical nature of the pulses is advantageous, our invention is also applicable to apparatus using asymmetrical, balanced pulses. As used herein, the term "substantially balanced" refers to the fact that current pulses of opposite polarity have sufficiently equal and opposite charging effect on tissue. In other words, pulses of one polarity substantially neutralize the charging effect of pulses of the opposite polarity so that deleterious charging is avoided.

The signal injector 46 has a storage capacitor 54 which is connected to a voltage source 56 through a switch S6. The voltage source 56 may be a battery or other power source conventionally used to provide electrical power within an implantable pacemaker. The magnitude of the voltage on the storage capacitor 54 may be a major determinant of the injector's current source compliance.

The indifferent electrode may be the can 60. The switch S6, and all of the other switches described herein, may be controlled by the microprocessor 14. The switch S6 is closed to connect the capacitor 54 to the voltage source 56 and to charge the capacitor. A constant current source 58 is connected between the capacitor 54 and a switch network 55. By measuring the voltage drop across the heart, as more particularly described hereafter, the impedance can therefore be easily computed. When a biphasic pulse pair is produced, the switch S6 is opened and four switches S1, S2, S3 and S4, are closed and opened under the control of the microprocessor 14.

To produce the first pulse 50, switches S1 and S2 are closed while switches S3 and S4 remain open. This connects a first side of the capacitor 54 and current source 58 through switch S1 to the lead 30 and electrode 31. After a selected duration, for example five microseconds, switches S1 and S2 are opened by the microprocessor 14 and switches S3 and S4 are closed. This connects the second side of the capacitor 54 through switch S3 to the lead 30 and electrode 31, reversing the polarity of the current pulse being applied.

Pulse pairs may be produced on the order of one hundred times per second but they may also be produced in other frequencies, for example, from two times per second to several hundred times per second. Their duration, therefore, is about one thousand times shorter than the charging period when the switch S6 is connected to the capacitor 54. Consequently, because of the relatively large size of the capacitor 54 and its comparatively long charging period compared to the amplitude and duration of the pulses, the electrical condition of the capacitor 54 (and the current source supply voltage) may be essentially constant.

Figure 4:
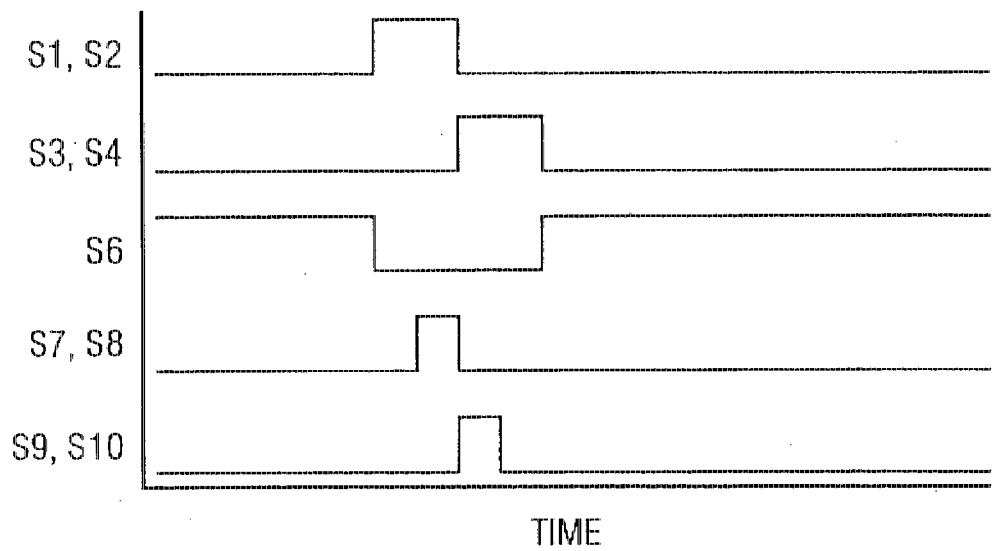
FIG. 4 is a timing diagram showing the duration of switch operation.

The voltages associated with the pulses of the biphasic pulse pair are detected through the detector 48 which derives a signal proportional to the voltage observed across electrodes connected to the detector 48. The detector 48 has two capacitors 62, 64 which are connected through four switches S7, S8, S9 and S10 to the lead 30. During the first pulse 50, when switches S1 and S2 of the injector 46 are closed, switches S7 and S8 of the detector 48 make contact to the lead 30 and electrode 31 through contacts 33 and 35. A second side of the first capacitor 62 is connectable to the sample-and-hold circuit 68. When the first pulse 50 is over, and switches S1 and S2 are opened, switches S7 and S8 connect to the sample-and-hold circuit 68 as also shown in FIG. 4. The duration of the sampling may occupy all or a portion of the duration of the injected current pulses, but the duration $T_D$ and the size $C_s$ of the sampling capacitors 62, 64 may be chosen so that $4 \times (Z_{LEAD} \times C_s)$ is less than or equal to $T_D$. Thus, at least three to four time constants are available for sampling. As a result, the sampling capacitor voltages are less sensitive to capacitive loading or timing uncertainties.

During the second pulse 52, when switches S3 and S4 are closed, switches S9 and S10 connect through the contacts 37 and 39 to the lead 30 and electrode 31 thereby connecting the second capacitor 64 to the electrodes. When the second pulse 52 ends and switches S3 and S4 are opened, switches S9 and S10 connect the first side of the second capacitor 64 to the sample-and-hold circuit 69. The sample-and-hold circuits 68 and 69 sample the voltages on the capacitors 62 and 64. Alternatively, the first and second capacitors 62, 64 themselves can act as sample-and-hold circuits.

The outputs of the sample-and-hold circuits 68 and 69 can be added in summer 71 or subtracted in a comparator or a summer 73 which outputs a signal indicative of the voltage difference between its inputs. Background effects such as the intrinsic electrical potentials from the heart, being common to both capacitors 62, 64, are eliminated by the subtractive combination. The resulting signal to the microprocessor 14 may be free of background effects. The subtractive combination signal is used to calculate the impedance of the heart using known techniques. This information can then be applied by the microprocessor 14 to, for example, select the most effective pacing rate.

The current pulse created by the injector 46 may be shunted by switch S11 through a resistive load 74. If desired, the lead 30 and the heart may be isolated to enable testing without any possible interference from heart signals, such as intracardiac electrogram pulses. This may be accomplished by opening switches S12 and S13 under control of the microprocessor 14.

The current pulses 50 and 52 are then selectively conducted through the resistive load 74 to create a voltage representation of the pulse amplitude and duration on capacitor 62 or 64. Then the voltage representations can be buffered and stored by sample-and-hold circuits 68 and 69. The resulting level may be summed by summer 71.

A number of failures could result in imbalanced pulses. The pulses shown in FIG. 5 may result from a shorted switch. While pulses of both polarities are produced, deleterious charging effects could result from the imbalanced amplitudes of the pulses of opposite polarity. The pulses shown in FIG. 6 may result from an open switch. In this case pulses of one polarity are eliminated. This increases the possibility of capturing the heart, potentially at a high rate, this possibly inducing an unintended ventricular fibrillation.

The switches S11, S12 and S13 are periodically operated to electrically isolate the lead 30 from the injector 46 and to connect the resistive load 74. Charge balance can then be checked with sufficient frequency to minimize the possibility of adverse affects arising from imbalanced pulses.

Figure 5:
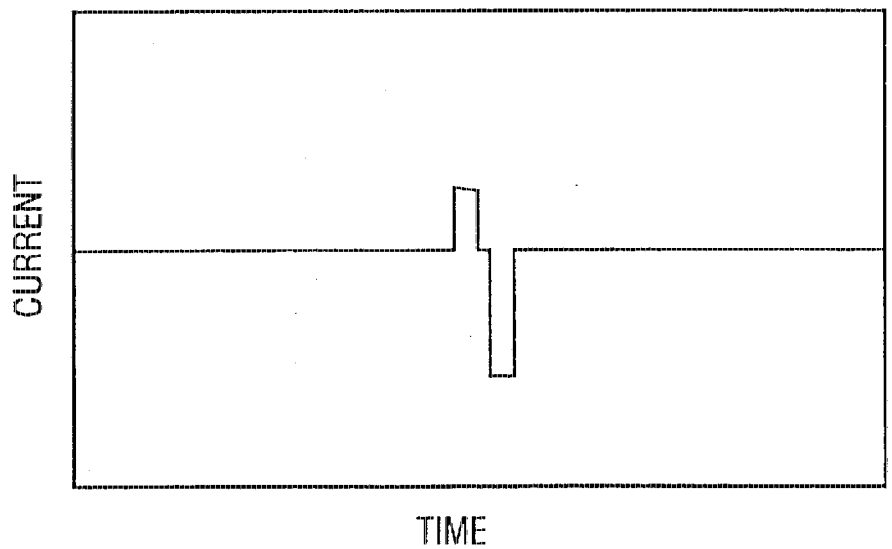
FIG. 5 shows an idealized plot of current versus time for an exemplary series of imbalanced biphasic pulses which could result if a switch were shorted.
Figure 6:
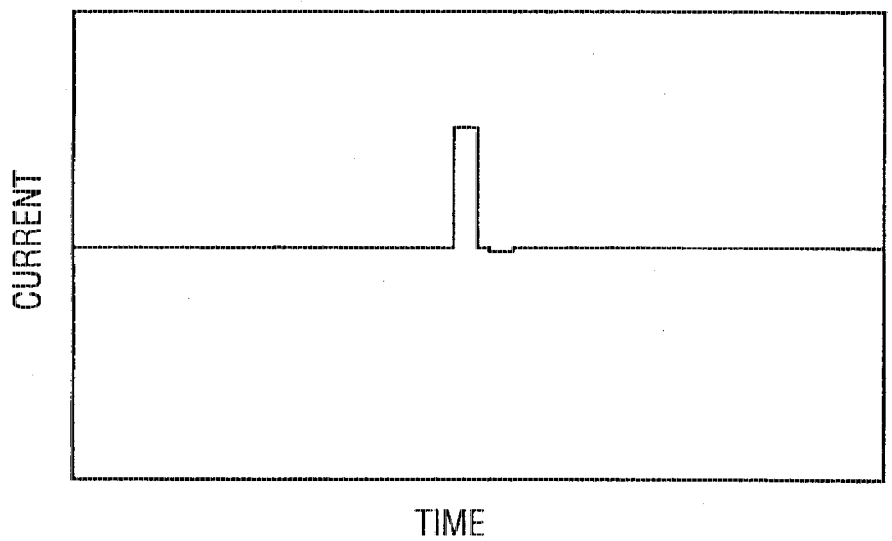
FIG. 6 shows an idealized plot of current versus time for an exemplary series of imbalanced pulses which would be the result of an open switch.

The summer 71 outputs a combined signal indicative of safe operation of the impedance measuring circuit 42. So long as the additively combined voltage signals representative of the current pulses are approximately zero, the impedance measuring circuit 42 is operating correctly. If imbalanced pulses are created, as illustrated in FIGS. 5 and 6, the sum of the voltage signals representative of the biphasic current pulses will not be approximately zero. This sum signal may be transmitted to the microprocessor 14 which may compare the sum signal to a predetermined level to determine the appropriate corrective action. For example, the impedance measuring circuit 42 may be disabled through switch control and an alternative measuring technique may be used in its place. While exact balancing of the current pulses may be advantageous, the present invention is not limited to the situation where the amplitude (and/or duration) of the current pulses of opposite polarity are exactly equal.

The operation of the impedance measuring circuitry can also be continuously monitored with switches S12 and S13 closed. However, in such case it may be necessary to control or blank the monitoring operation to avoiding interference from cardiac signals such as intracardiac electrogram pulses. This can be accomplished, for example, by conventional signal detection coupled with microprocessor 14 control.

Figure 7:
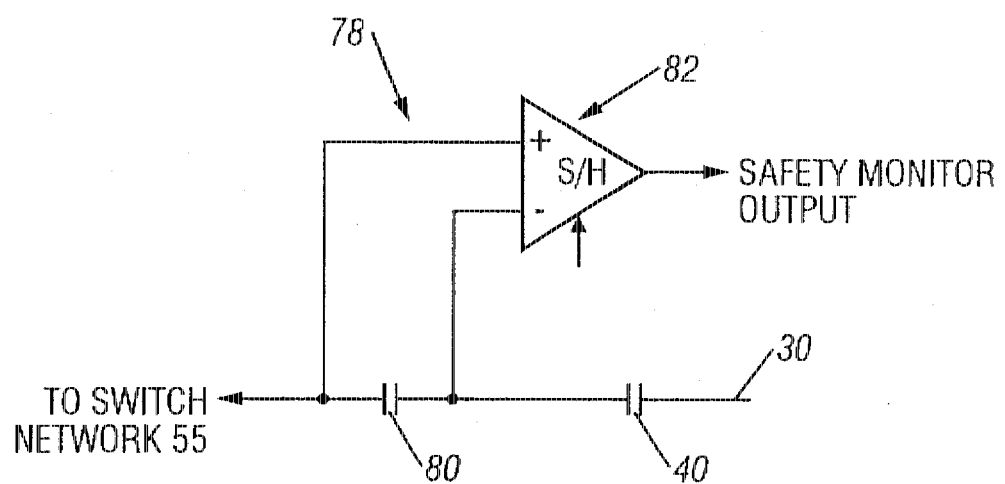
FIG. 7 is a circuit diagram of an embodiment of another monitoring circuit in accordance with our invention.

Another monitoring embodiment in accordance with our invention is shown in FIG. 7. The circuit 78 monitors the net charge that is deposited into the capacitor 80 by the injected pulses 50, 52. This net charge is indicative of the degree of imbalance between the pulses of opposite polarity. The monitored capacitor 80 is illustrated in FIG. 7 as being located adjacent to the coupling capacitor 40. It may, however, be located elsewhere in series with the biphasic current path to facilitate monitoring or it may even be used as the DC blocking capacitor, thereby eliminating the need for an extra capacitor.

The size of the capacitor 80 may be beneficially selected to be large enough to allow efficient transmission of balanced biphasic current pulses but small enough so that any charge imbalance rapidly accumulates voltage. In one advantageous embodiment, the capacitor 80 is from about 0.01 to 1 microfarad. Rapid voltage buildup on the capacitor 80 facilitates rapid detection of any charge imbalance. The voltage on each side of the capacitor 80 is applied to each of the inputs of a sample-and-hold circuit 82. If a net charge build-up of either polarity is created on the capacitor 80 as a result of an imbalance between biphasic pulses, an output signal is transmitted to the microprocessor 14. The microprocessor 14 then implements appropriate corrective action.

When the circuit 42 operates under no-fault conditions, almost no charge integration occurs in the monitored capacitor 80. On the other hand, fault conditions cause the integration of charge by capacitor 80, which can be monitored by measuring the voltage across this capacitor after pulses are delivered.

Under no-fault conditions, some charge is integrated into the monitored capacitor 80 due to asymmetries, unbalanced intracardiac electrogram signals and electrode polarization potentials. However, charge is quickly accumulated into the capacitor 80 by the delivery of unbalanced biphasic current pulses. This facilitates a real-time assessment of the balance of charge transferred by the pulse phases.

The selection of an appropriate voltage source 56 together with the monitoring of the capacitor 80 can provide an inherent safety mechanism. The capacitor 80 can limit current when the voltage on capacitor 80 approaches the magnitude of voltage of the source 56. This prevents the current pulses from being applied to the heart tissue under imbalanced conditions.

The present invention can also be used in connection with monitoring implanted cardiac sensors that measure varying impedance as a function of other body conditions such as metabolites or dissolved gases.

Our invention may be embodied in other specific forms without departing from the spirit or essential characteristics thereof. The foregoing description is, therefore, to be viewed in all respects as illustrative and not restrictive. The scope of our invention is defined by the appended claims.

We claim as our invention:

1. A cardiac stimulation apparatus comprising:
   a stimulator for producing a stimulating pulse to stimulate a patient's heart;
   an impedance measuring circuit for measuring impedance within the patient's body, said impedance measuring circuit including
      a signal generator for producing a biphasic current pulse pair, said pulse pair having a first pulse having current flowing in a first direction and a second pulse having current flowing in a second direction, means for electrically transmitting said pulse pair through at least a portion of the patient's body, and
   means for determining impedance from said pulse pair;
   means responsive to said impedance measuring circuit for controlling said stimulator;
   a monitor comprising a test load for selectively receiving said pulse pair and means for comparing said first and second pulses when applied across said test load; and
   means responsive to said monitor for controlling said impedance measuring circuit.

2. The apparatus of claim 1 wherein said monitor includes a circuit for generating voltage signals representative of the amplitude of both of said pulses of at least one pulse pair and wherein said means for comparing said first and second pulses includes means for comparing said voltage signals.

3. The apparatus of claim 2 including a first circuit for generating a first voltage signal representative of the amplitude of said first pulses and a second circuit for generating a second voltage signal of opposite polarity indicative of the amplitude of said second pulses and wherein said means for comparing said first and second pulses includes means for comparing said voltage signals.

4. The apparatus of claim 3 wherein said means for comparing includes a summer connected to said first and second circuits to add said first and second voltage signals and a comparator for comparing said first and second voltage signals to a predetermined standard.

5. The apparatus of claim 4 wherein said first and second voltage signals are also representative of the duration of said pulses.

6. The apparatus of claim 2 wherein said test load includes a capacitor connected to be in series with said portion of the patient's body and said signal generator when said means for transmitting said pulse pair is connected to said patient's body and wherein said means for comparing comprises a comparator connected in parallel with said capacitor.

7. The apparatus of claim 6 wherein said capacitor is a DC-blocking capacitor connected to said simulator.

8. The apparatus of claim 6 wherein said capacitor is from 0.01 to 1 microfarad.

9. The apparatus of claim 2 wherein said test load includes a resistive load connected to be in parallel with said portion of the patient's body and said signal generator when said means for transmitting said pulse pair is connected to said patient's body.

10. The apparatus of claim 1 wherein said test load continuously receives said first and second pulses.

11. The apparatus of claim 1 wherein said test load periodically receives said first and second pulses.

12. The apparatus of claim 11 including means for disconnecting said signal generator from said means for electrically transmitting said pulse pair when said monitor is comparing said first and second pulses.

13. An impedance measuring apparatus for use in controlling a cardiac stimulator apparatus, said measuring apparatus comprising:
   a circuit for generating biphasic current pulse pairs;
   means for applying said pulse pairs to a portion of said patient's body;
   means for determining impedance of said portion of said patient's body from said applied pulse pairs; and
   monitor means connected to said circuit for determining whether each of said current pulse pairs is substantially electrically balanced.

14. The apparatus of claim 13 wherein said means for applying comprises a lead for connection to the heart.

15. The apparatus of claim 14 wherein said monitor means comprises means for continuously monitoring whether said current pulses are substantially balanced.

16. The apparatus of claim 14 including a switching system connected between said monitor means and said circuit means, said system conducting selected current pulse pairs to said monitor means.

17. The apparatus of claim 16 wherein said switching system disconnects said means for applying said pulse pairs to said portion of a patient's body when said selected pulse pairs are conducted to said monitor means.

18. A method for cardiac stimulation comprising the steps of:

stimulating the patient's heart;

measuring impedance within the patient's body, said measuring step including the steps of producing a biphasic current pulse pair, said pulse pair having a first pulse having current flowing in a first direction and a second pulse having current flowing in a second direction and transmitting said pulse pairs through a connection to at least a portion of the patient's body;

controlling the stimulating of the patient's heart as a function of said measure impedance;

monitoring at least some of said first and second pulses to determine whether said pulse pairs are not substantially electrically balanced; and adjusting said current pulse pairs in response to said determination.

19. The method of claim 18 wherein the step of monitoring said pulse pairs comprises monitoring substantially all said pulse pairs.

20. The method of claim 18 including the step of disconnecting the connection to the portion of the patient's body when monitoring said pulse pairs.

21. The method of claim 18 including the steps of detecting intrinsic signals in the body of the patient and blanking the monitoring of said pulse pairs in response to the detection of said signals.

22. The method of claim 21 wherein the step of detecting intrinsic signals includes detecting intracardiac signals.

23. The method of claim 18 wherein the step of monitoring includes the steps of producing signals proportional to the amplitude and duration of each pulse and comparing said signals.

24. The method of claim 23 wherein the step of comparing said signals includes the step of combining signals corresponding to said first pulses with signals corresponding to said second pulses.

25. The method of claim 24 wherein the step of combining said signals includes adding said signals.

26. The method of claim 18 including the step of terminating the impedance measuring when said monitoring determines that a pulse pair is not substantially balanced.

\* \* \* \* \*